United States Patent
Wang et al.

(10) Patent No.: US 11,965,842 B2
(45) Date of Patent: Apr. 23, 2024

(54) METHOD, DEVICE, AND SYSTEM FOR DETECTING SWEETNESS OF FRUIT, AND STORAGE MEDIUM

(71) Applicant: University of Nottingham Ningbo China, Ningbo (CN)

(72) Inventors: Chengbo Wang, Ningbo (CN); Xinpei Wang, Ningbo (CN); Jichang Zhang, Ningbo (CN)

(73) Assignee: University of Nottingham Ningbo China, Ningbo (CN)

( * ) Notice: Subject to any disclaimer, the term of this patent is extended or adjusted under 35 U.S.C. 154(b) by 124 days.

(21) Appl. No.: 17/775,235

(22) PCT Filed: Nov. 6, 2020

(86) PCT No.: PCT/CN2020/127203
§ 371 (c)(1),
(2) Date: May 6, 2022

(87) PCT Pub. No.: WO2021/089001
PCT Pub. Date: May 14, 2021

(65) Prior Publication Data
US 2022/0373488 A1    Nov. 24, 2022

(30) Foreign Application Priority Data
Nov. 8, 2019  (CN) ................... 201911089371.0

(51) Int. Cl.
*G01N 24/08*    (2006.01)
*G01N 33/02*    (2006.01)

(52) U.S. Cl.
CPC ........... *G01N 24/08* (2013.01); *G01N 33/025* (2013.01)

(58) Field of Classification Search
CPC .......................... G01N 24/08; G01N 33/025
See application file for complete search history.

(56) References Cited

U.S. PATENT DOCUMENTS

| 2012/0219507 A1 | 8/2012 | Santosh et al. |
| 2016/0202338 A1* | 7/2016 | Kimura ............ G01R 33/5608 |
| | | 324/309 |

FOREIGN PATENT DOCUMENTS

| CN | 201548524 U | 8/2010 |
| CN | 205003075 U | 1/2016 |

(Continued)

OTHER PUBLICATIONS

International Search Report dated Jan. 27, 2021 in connection with International Application No. PCT/CN2020/127203.
(Continued)

*Primary Examiner* — Gregory H Curran
(74) *Attorney, Agent, or Firm* — Wolf, Greenfield & Sacks, P.C.

(57) ABSTRACT

A method (100), a device (400), and a system for detecting the sweetness of fruit, and a storage medium. The method (100) comprises: using magnetic resonance diffusion weighted imaging to acquire an apparent diffusion coefficient (ADC) of fruit to be detected when same is undamaged (S110); determining an effective ADC of said fruit according to the ADC of said fruit (S120); and determining the sweetness of said fruit according to the effective ADC (S130). The ADC of fruit to be detected may be acquired on the basis of magnetic resonance imaging when said fruit is undamaged, and the ADC is used to determine the sweetness of the fruit, thus achieving non-destructive and reliable fruit sweetness detection.

19 Claims, 2 Drawing Sheets

(56) References Cited

FOREIGN PATENT DOCUMENTS

| | | | |
|---|---|---|---|
| CN | 105866050 A | 8/2016 |
| CN | 106525892 A | 3/2017 |
| CN | 206161593 U | 5/2017 |
| CN | 107860722 A | 3/2018 |
| CN | 107949325 A | 4/2018 |
| CN | 108369196 A | 8/2018 |
| CN | 108734163 A | 11/2018 |
| CN | 111366600 A | 7/2020 |
| JP | H06-288943 A | 10/1994 |
| JP | H09-196869 A | 7/1997 |
| JP | 2006-266950 A | 10/2006 |

OTHER PUBLICATIONS

Chinese Notification to Grant Patent Right dated Jan. 11, 2022 in connection with Chinese Application No. 201911089371.0.
Melado-Herreros et al., On-line MRI sequences for the evaluation of apple internal quality. InsideFood Symposium. Apr. 9-12, 2013. 6 pages.
Gao et al., Metabolic Flux Analysis of Hybridoma Cells. Chinese Journal of Biotechnology. Nov. 2000;16(6):741-6.

\* cited by examiner

METHOD, DEVICE, AND SYSTEM FOR DETECTING SWEETNESS OF FRUIT, AND STORAGE MEDIUM

CROSS-REFERENCE TO RELATED APPLICATIONS

This application is a 35 U.S.C. § 371 National Phase filing of International Application No. PCT/CN2020/127203, filed on Nov. 6, 2020, entitled "METHOD, DEVICE, AND SYSTEM FOR DETECTING SWEETNESS OF FRUIT, AND STORAGE MEDIUM," which claims priority to and the benefit of Chinese Patent Application No. 201911089371.0, filed on Nov. 8, 2019. The entire contents of these applications are incorporated herein by reference in their entirety.

TECHNICAL FIELD

The present invention relates to the field of food detection, in particular to a method, a device and a system for detecting sweetness of a fruit and a storage medium.

BACKGROUND

Sweetness is one of the most important indexes for measuring the quality of fruit and has been widely concerned as an important parameter for quality classification and rating all the time.

At present, prior methods for detecting sweetness of a fruit mainly include destructive chemical detection and non-destructive near-infrared spectroscopy. As leading to loss of some fruit products, the destructive chemical detection method can only detect fruits by sampling, which cannot meet the requirement for large-scale product detection. Non-destructive near-infrared spectroscopy, as a kind of green non-destructive detection means, is widely applied to evaluation and rating on sweetness of a fruit, but still has the following deficiencies: 1) with infrared detection, only the sweetness of pulp within 5 mm from the peel can be determined, while the sweetness of thick-skin fruit and the interior of bigger fruit cannot be detected; and 2) in order to ensure the detection quality, it is required a conveyor belt to be kept at a low speed, and only one fruit can be detected each time, so the high-speed detection requirement cannot be met.

Therefore, there is an urgent need for a novel technology for detecting sweetness of a fruit to solve the above problems.

BRIEF SUMMARY

Embodiments of the present invention are provided in consideration of the above-mentioned problems. The embodiments of the present invention provide a method, a device and a system for detecting sweetness of a fruit and a storage medium.

A method for detecting sweetness of a fruit is provided according to an aspect of the invention. The method for detecting sweetness of a fruit comprises: nondestructively acquiring apparent diffusion coefficients of the fruit to be detected by means of magnetic resonance diffusion weighted imaging (DWI); determining an effective apparent diffusion coefficient of the fruit to be detected according to the apparent diffusion coefficients of the fruit to be detected; and determining the sweetness of the fruit to be detected according to the effective apparent diffusion coefficient.

Exemplarily, the method further comprises: nondestructively acquiring apparent diffusion coefficients of a fruit sample by means of magnetic resonance diffusion weighted imaging; determining an effective apparent diffusion coefficient of the fruit sample according to the apparent diffusion coefficients of the fruit sample; detecting sample sweetness of the fruit sample; and establishing a first sweetness detection model according to the effective apparent diffusion coefficient and the sample sweetness of the fruit sample, wherein the first sweetness detection model represents a correlation between the sweetness and the effective apparent diffusion coefficient; wherein the sweetness of the fruit to be detected is determined according to the effective apparent diffusion coefficient by using the first sweetness detection model.

Exemplarily, the first sweetness detection model is expressed as $Y=a1*x+b1$, wherein Y represents the sweetness; x represents the effective apparent diffusion coefficient; and a1 and b1 are parameters in the first sweetness detection model.

Exemplarily, the method further comprises: nondestructively acquiring apparent diffusion coefficients of a fruit sample and acquiring an apparent diffusion coefficient of a first reference object at the same time by means of magnetic resonance diffusion weighted imaging; determining an effective apparent diffusion coefficient of the fruit sample according to the apparent diffusion coefficients of the fruit sample; detecting sample sweetness of the fruit sample; and establishing a second sweetness detection model according to the apparent diffusion coefficient of the first reference object and the effective apparent diffusion coefficient and the sample sweetness of the fruit sample, wherein the second sweetness detection model represents a correlation between the sweetness of the fruit and two items, the effective apparent diffusion coefficient of the fruit and the apparent diffusion coefficient of the reference object; wherein an apparent diffusion coefficient of a second reference object is acquired while the apparent diffusion coefficients of the fruit to be detected are nondestructively acquired; the second reference object is a same substance as the first reference object; and the sweetness of the fruit to be detected is determined further according to the apparent diffusion coefficient of the second reference object and by using the second sweetness detection model.

Exemplarily, the second sweetness detection model is expressed as $Y=a2*x/x0+b2$, wherein Y represents the sweetness of the fruit; x represents the effective apparent diffusion coefficient of the fruit; x0 represents the apparent diffusion coefficient of the reference object; and a2 and b2 are parameters in the second sweetness detection model.

Exemplarily, the reference object is water.

Exemplarily, the apparent diffusion coefficients are expressed by an apparent diffusion coefficient image; and determining the effective apparent diffusion coefficient of the fruit to be detected according to the acquired apparent diffusion coefficients comprises: performing image segmentation on the apparent diffusion coefficient image to determine a region of interest within pulp of the fruit to be detected, and calculating an average of values of pixels in the region of interest as the effective apparent diffusion coefficient.

A device for detecting sweetness of a fruit is provided according to another aspect of the invention. The device for detecting sweetness of a fruit comprises: an imaging module, for nondestructively acquiring apparent diffusion coefficients of the fruit to be detected by means of magnetic resonance diffusion weighted imaging; a calculation module, for determining an effective apparent diffusion coefficient of the fruit to be detected according to the apparent diffusion coefficients of the fruit to be detected; and a sweetness determining module, for determining the sweetness of the fruit to be detected according to the effective apparent diffusion coefficient.

A system for detecting sweetness of a fruit is provided according to yet another aspect of the invention. The system for detecting sweetness of a fruit comprises a processor and a memory, wherein computer program instructions are stored in the memory which are configured to perform the above method for detecting the sweetness of the fruit when being operated by the processor.

A storage medium is provided according to yet another aspect of the invention. The storage medium stores program instructions which are configured to perform the above method for detecting the sweetness of the fruit, when being operated.

According to the above method, the device, the system for detecting the sweetness of the fruit and the storage medium, the apparent diffusion coefficients of the fruit are nondestructively acquired on the basis of magnetic resonance imaging, and the sweetness of the fruit is determined based on the apparent diffusion coefficients, so that non-destructive and reliable detection on the sweetness of the fruit is achieved. Additionally, multiple fruits can be accurately detected at one time in the embodiments of the present invention.

The above description is only an overview of the technical solutions of the embodiments of the present invention. In order to understand the technical solutions of the present invention more clearly and implement them according to the content of the description, and in order to make the above and other objects, features and advantages of the present invention more obvious and easy to understand, the specific embodiments of the present invention are given below.

BRIEF DESCRIPTION OF THE DRAWINGS

The above and other objects, features, and advantages of the present invention will become more apparent from more detailed description of embodiments of the present invention in conjunction with the accompanying drawings. The accompanying drawings serve to provide a further understanding of the embodiments of the present invention, constitute a part of the specification, serve to explain the present invention, together with the embodiments of the present invention, and do not constitute a limitation to the present invention. In the accompanying drawings, identical reference numerals generally represent identical components or steps.

DETAILED DESCRIPTION OF THE DISCLOSURE

For making objectives, technical solutions and advantages of the present invention more apparent, exemplary embodiments according to the present invention will be described in detail below with reference to the accompanying drawings. Obviously, the described embodiments are only parts of instead all embodiments of the present invention, and it is to be understood that the present invention is not limited by the exemplary embodiments described herein. Based on the embodiments of the present invention described herein, all other embodiments obtained by those skilled in the art without inventive steps should fall within the scope of the protection of the present invention.

In order to solve the above problems, the present invention provides a method for detecting sweetness of a fruit. The method for detecting the sweetness of the fruit may be achieved on the basis of magnetic resonance diffusion weighted imaging (DWI) technology. At present, magnetic resonance imaging is mainly used in the field of medical diagnosis. In conventional magnetic resonance imaging, radio frequency pulses are used for exciting magnetization vectors in an imaging target. The spatial location information of the magnetization vectors is labeled by phase gradient encoding and frequency encoding and an image is reconstructed by Fourier transform. The magnetic resonance imaging method is a kind of non-destructive imaging means, capable of providing a variety of high-resolution target internal structural diagrams by weighted imaging, including diffusion weighted imaging. Magnetic resonance diffusion weighted imaging is a magnetic resonance imaging technology widely applied to researching the diffusion phenomenon of water molecules in substances. By using a diffusion speed of water molecules in an imaging target, a diffusion coefficient of the water molecules in the imaging target may be calculated. A large number of experimental experiments have been already conducted to detect the sweetness of a fruit; and experiment results show that the sweetness of the fruit has a strong correlation with apparent diffusion coefficients thereof.

Figure 1:
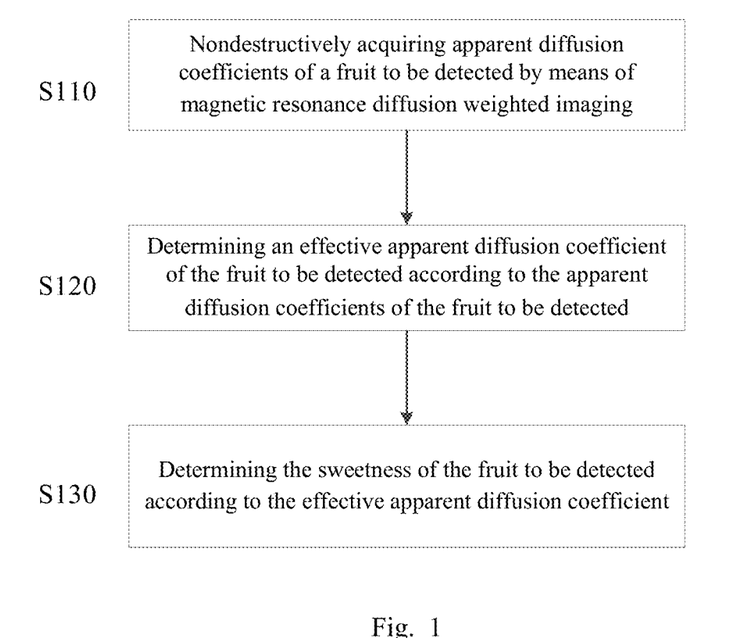
FIG. 1 shows a schematic flow chart of a method for detecting sweetness of a fruit according to an embodiment of the present invention.

FIG. 1 is a schematic flow chart of a method 100 for detecting sweetness of a fruit according to an embodiment of the present invention.

As shown in FIG. 1, the method 100 includes a step S110, a step S120 and a step S130.

In step S110, apparent diffusion coefficients of the fruit to be detected are nondestructively acquired by means of magnetic resonance diffusion weighted imaging.

Magnetic resonance diffusion weighted imaging is based on motion of water molecules which may directly embody the rate of diffusion of the water molecules in the imaging target. Sugar molecules, whether monosaccharide molecules, disaccharide molecules or polysaccharide molecules, in the fruit may affect motion of the water molecules in the fruit. In general, sugar molecules can make the diffusion speed of water molecules significantly lower.

The apparent diffusion coefficient is an index for the rate of diffusion that occurs when soluble substance passes through permeable medium. The diffusion coefficient is related to the structure of the medium, the uniformity of permeating paths, an average permeating velocity and the physicochemical properties of a fluid. As previously mentioned, the rate of diffusion of the water molecules is affected by the sugar molecules in the fruit; and generally, the higher the concentration of the sugar molecules is, the lower the rate of diffusion is.

It is can be understood that the sweetness of the fruit is mainly decided by the sugar molecules in the fruit.

On the basis of the above analysis, the sweetness of the fruit to be detected may be determined by performing magnetic resonance diffusion weighted imaging on it in case that it is intact.

FIG. 2A, FIG. 2B, FIG. 2C and FIG. 2D respectively are an optical image of a fruit to be detected (an orange), a T2 weighed image in case that a DW-MRI diffusion sensitive parameter of the fruit is equal to 0, a diffusion weighed image in case that the DW-MRI diffusion sensitive parameter of the fruit is relatively high and an ADC image of the fruit according to an embodiment of the present invention.

Figure 2A:
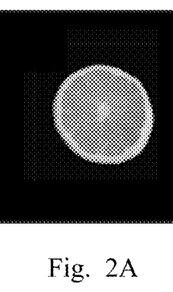
FIG. 2A, FIG. 2B, FIG. 2C and FIG. 2D respectively show an optical image of a fruit, a T2 weighed image in case that a DW-MRI diffusion sensitive parameter of the fruit is equal to 0, a diffusion weighed image in case that the DW-MRI diffusion sensitive parameter of the fruit is relatively high and an ADC image of the fruit according to an embodiment of the present invention.
Figure 2B:
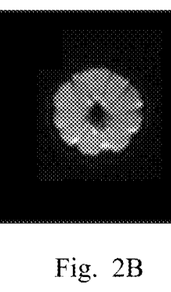
Figure 2C:
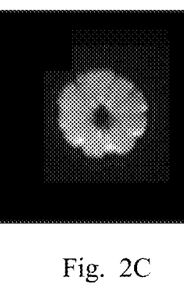

Illustratively, the apparent diffusion coefficients may be acquired by magnetic resonance imaging for the fruit to be detected under the condition that the intensity of the magnetic field is equal to 0 (as shown in FIG. 2B) and magnetic resonance imaging for the fruit to be detected under the condition of high intensity of the magnetic field (as shown in FIG. 2C). Specifically, the apparent diffusion coefficient of each position of the fruit to be detected may be calculated according to corresponding values of pixels in the two images.

For example, the apparent diffusion coefficient ADC of the fruit to be detected is calculated according to the formula (1).

$$ADC = \ln(S_0/S_1)/b \qquad (1)$$

wherein b represents the diffusion sensitive parameter in the diffusion weighed image, $S_0$ represents the signal intensity of a magnetic resonance image with b=0 (without an external diffusion magnetic field pair), and $S_1$ represents the signal intensity of a magnetic resonance image under the condition of high magnetic field intensity. Increase in value of b is beneficial to detecting a finer diffusion phenomenon. The apparent diffusion coefficient of each portion of the fruit to be detected may be calculated point to point by using magnetic resonance diffusion weighted imaging according to the formula (1). The apparent diffusion coefficients may be represented by a matrix.

Figure 2D:
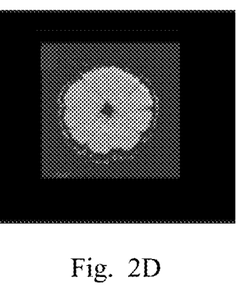

Alternatively, the fruit to be detected may be imaged directly by using an advanced magnetic resonance imaging device, and then an apparent diffusion coefficient image is acquired directly, as shown in FIG. 2D. Different apparent diffusion coefficients are represented by different values of pixels in the apparent diffusion coefficient image. The pixel value of each pixel represents the apparent diffusion coefficient of a corresponding position of the fruit to be detected.

In the step S110, the fruit to be detected is imaged nondestructively, to acquire the apparent diffusion coefficients thereof. As mentioned above, the apparent diffusion coefficients of various portions of the fruit to be detected are different and are related to the detected portions. For example, in regard to oranges, the apparent diffusion coefficients of the skin portion and the orange fiber gathering portion in the center are smaller; while the apparent diffusion coefficients of the pulp portion are larger.

Step S120, an effective apparent diffusion coefficient of the fruit to be detected is determined according to the apparent diffusion coefficients of the fruit.

A fruit generally has inedible portions such as skin, a cavity and a core, and the sweetness of the inedible portions, for example, the skin portion of an orange, does not affect the quality of the fruit. In addition, the fruit may have been rotten and the like in the preservation or transportation process. Then, the rotten portion of the fruit should not be taken as a detection portion. The apparent diffusion coefficients of these portions are not worth being considered and may further bring adverse effect on accurate determination of the sweetness of the fruit. Therefore, in the step S120, the effective apparent diffusion coefficient of the fruit to be detected is determined according to the apparent diffusion coefficients of the fruit. The effective apparent diffusion coefficient is a single numerical value.

Illustratively, the apparent diffusion coefficients of the portions such as the skin, the cavity, the core and so on, of the fruit to be detected are abandoned, and an average of the rest apparent diffusion coefficients is calculated to acquire the effective apparent diffusion coefficient.

Step S130, the sweetness of the fruit to be detected is determined according to the effective apparent diffusion coefficient.

As previously mentioned, the sweetness of the fruit has a strong correlation with the apparent diffusion coefficients thereof. After a great number of experiments, it is discovered that the effect of solid pulp tissues of the fruit on the rate of diffusion of the water molecules therein is not very significant. Therefore, the sweetness of the fruit may be determined on the basis of the apparent diffusion coefficients acquired nondestructively, without having to juice the fruit. The effective apparent diffusion coefficient of the fruit to be detected is determined on the basis of the apparent diffusion coefficients acquired nondestructively, and the sweetness of the fruit can be determined by using a mapping relationship between the effective apparent diffusion coefficient and the sweetness of the fruit.

In the above method for detecting the sweetness of the fruit, the apparent diffusion coefficients of the fruit are nondestructively acquired on the basis of magnetic resonance imaging, and the sweetness of the fruit is determined based on the apparent diffusion coefficients, so that nondestructive and reliable detection on the sweetness of the fruit is achieved.

As previously mentioned, the apparent diffusion coefficients acquired in step S110 may be represented by an apparent diffusion coefficient image. Illustratively, the step S120 of determining the effective apparent diffusion coefficient according to the acquired apparent diffusion coefficients may include the following steps. Firstly, image segmentation is performed on the apparent diffusion coefficient image, to determine a region of interest containing pulp of the fruit to be detected. For example, the apparent diffusion coefficient image may be segmented by using a region growing image segmentation method. An average of values of all pixels in the apparent diffusion coefficient image is calculated, to determine a seed pixel. On the basis of the seed pixel, surrounding pixels are continuously added according to a certain rule, and a purpose is finally achieved that all the pixels corresponding to the effective portion of the fruit are combined into one region. The acquired region is the desirable region of interest. Then, an average of the values of pixels in the region of interest is calculated, to serve as the effective apparent diffusion coefficient of the fruit to be detected. The sweetness of the fruit can be more ideally determined on the basis of the effective apparent diffusion coefficient. According to the technical solution, data is effectively utilized, and the interference factor is avoided.

Alternatively, statistical analysis may be performed on all the apparent diffusion coefficients acquired in step S110. On the basis of probability distribution of the apparent diffusion coefficients, shown by the statistical analysis result, the apparent diffusion coefficients with the probability higher than a preset probability threshold are averaged, and the average value may be taken as the effective apparent diffusion coefficient.

Illustratively, the process for determining the sweetness of the fruit according to the effective apparent diffusion coefficient may be realized by a sweetness detection model. The sweetness detection model represents a mathematical correlation between the effective apparent diffusion coefficient and the sweetness of the fruit, which may be expressed by a functional expression. Alternatively, the method for detecting the sweetness of the fruit further includes the following steps for establishing the sweetness detection model. The subsequent step for determining the sweetness of the fruit to be detected according to the effective apparent diffusion coefficient is realized by the sweetness detection model.

In an example, the step of establishing the sweetness detection model includes the following steps.

In step S101, apparent diffusion coefficients of a fruit sample are nondestructively acquired by means of magnetic resonance diffusion weighted imaging.

In step S102, an effective apparent diffusion coefficient of the fruit sample is determined according to the apparent diffusion coefficients of the fruit sample.

In step S103, the sample sweetness of the fruit sample is detected.

In step S104, a first sweetness detection model is established according to the effective apparent diffusion coefficient and the sample sweetness of the fruit sample, wherein the first sweetness detection model represents a correlation between the sweetness and the effective apparent diffusion coefficient.

The fruit sample and the fruit to be detected are of the same kind, for example, are both oranges. In order to acquire a more accurate first sweetness detection model, the number of the fruit samples detected herein may be more than a preset number threshold. Thus, the acquired first sweetness detection model can more effectively represent the universal correlation between the effective apparent diffusion coefficient and the sweetness of the fruit. The implementation processes of the step S101 and step S102 are similar to those of the step S110 and step S120, which will not be described herein for brevity. In step S103, any prior method for detecting the sweetness of the fruit may be employed. For example, a method for destructively detecting sweetness of the fruit is employed, so that the sweetness of the fruit sample is accurately acquired. In step S104, sample points in a coordinate system may be determined according to the effective apparent diffusion coefficients determined in step S102 and the sweetness detected in the step S103, of all the fruit samples, and fitting is performed on the basis of the sample points to obtain a function curve of the effective apparent diffusion coefficient versus the sweetness of the fruit samples, i.e. the first sweetness detection model.

According to the above technical solution, the first sweetness detection model representing the correlation between the sweetness and the effective apparent diffusion coefficient of the fruit is determined by using the fruit samples. On the basis of the sweetness detection model, the sweetness of the fruit can be accurately determined.

After a great amount of experiments, it is shown that the effective apparent diffusion coefficient has a linear correlation with the sweetness of the sample. The first sweetness detection model may be expressed as $Y=a1*x+b1$, wherein Y represents the sweetness of the fruit; x represents the effective apparent diffusion coefficient of the fruit; and $a1$ and $b1$ are parameters in the first sweetness detection model.

Figure 3:
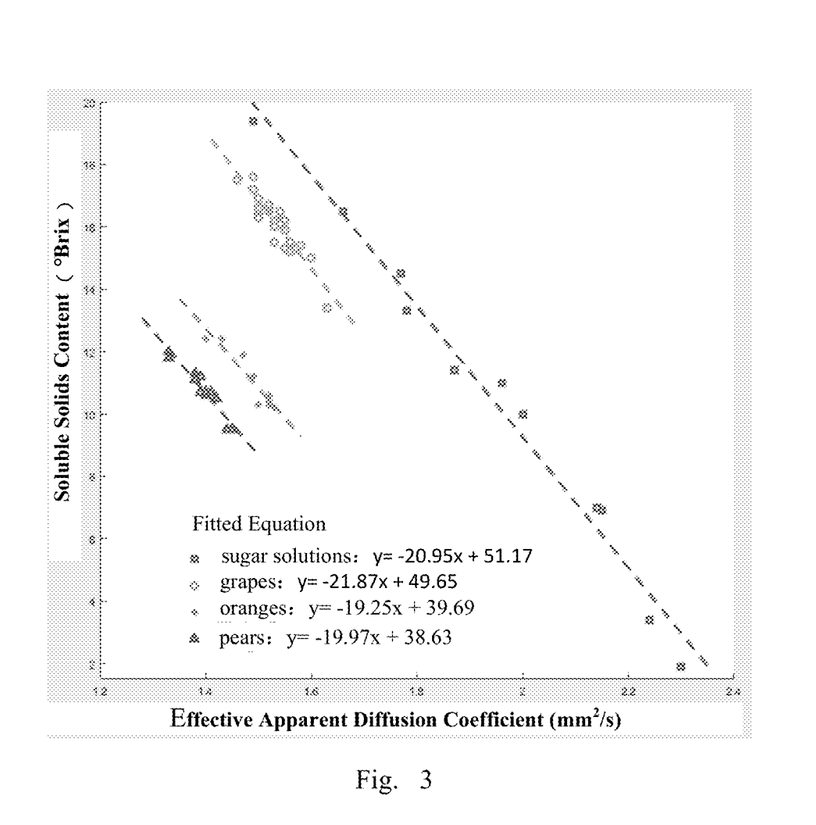
FIG. 3 shows a schematic diagram of fitting a first sweetness detection model according to the sample sweetness and an effective apparent diffusion coefficient of a fruit sample according to an embodiment of the present invention.

FIG. 3 is a schematic diagram of fitting a first sweetness detection model according to the sample sweetness and an effective apparent diffusion coefficient of a fruit sample according to an embodiment of the present invention. The first sweetness detection models shown in FIG. 3 involve various fruits, including grapes, oranges and pears. FIG. 3 further shows the first sweetness detection model established according to sugar solutions. In FIG. 3, soluble solids content refers to sugar. It can be seen that the sweetness of the fruit sample has a linear negative correlation with the effective apparent diffusion coefficient thereof; and there is a small difference among slopes of curves of the first sweetness detection models of different kinds of fruit samples.

It is can be understood that the higher the sweetness of the fruit is, the thicker the sugar solution macroscopically appears, the microcosmic interpretation of which is that diffusion of the water molecules is more greatly limited, that is, the apparent diffusion coefficient is lower. Therefore, the sweetness of the fruit sample has a linear negative correlation with the effective apparent diffusion coefficient thereof, wherein the parameter $a1$ is a negative number. As the major component affecting diffusion of the water molecules in various fruit samples is sugar, there is a small difference among the slopes of curves of the first sweetness detection models of different kinds of fruit samples, and there is a relatively small difference among values of $a1$ in the first sweetness detection models of various samples.

Illustratively, the parameters $a1$ and $b1$ may be set from experience according to the above description, so as to omit the above complicated operations for establishing the first sweetness detection model.

It is well-known that increased temperature may make the molecules move faster, which enables the speed of diffusion of the water molecules to be correspondingly higher. For example, if one drop of ink drops into cold water and another one drop of ink drops into boiled water, the rate of diffusion of the ink in the boiled water is higher than that of the ink in the cold water, the reason of which is that the motion speed of the water molecules in the boiled water is higher than that in the cold water. Apparently, a difference, caused by the temperatures, between the apparent diffusion coefficients is ignored according to detection results of the first sweetness detection model. In order to avoid the effect of a temperature difference on the accuracy of the detection result, a second sweetness detection model may be established according to the following steps.

In step S101', apparent diffusion coefficients of a fruit sample are nondestructively acquired and an apparent diffusion coefficient of a first reference object is acquired at the same time by means of magnetic resonance diffusion weighted imaging.

In step S102', an effective apparent diffusion coefficient of the fruit sample is determined according to the apparent diffusion coefficients thereof.

In step S103', the sample sweetness of the fruit sample is detected.

In step S104', a second sweetness detection model is established according to the apparent diffusion coefficients of the first reference object and the effective apparent diffusion coefficient and the sample sweetness of the fruit sample, wherein the second sweetness detection model represents a correlation between the sweetness of the fruit and two items, the effective apparent diffusion coefficient of the fruit and the apparent diffusion coefficient of the reference object.

In the step S101', the apparent diffusion coefficient of the first reference object is acquired while the apparent diffusion coefficients of the fruit sample are acquired. During magnetic resonance diffusion weighted imaging, the first reference object may be placed near the fruit sample. It is can be understood that the first reference object and the fruit sample may be considered to be at a consistent temperature as being in the same environment. Step S102' is similar to step S102, and the effective apparent diffusion coefficient of the fruit sample is determined. As the first reference object may be a kind of substance with the uniformity in apparent diffusion coefficient, there may be no need for executing operation of step S102' thereon. Step S103' is similar to step S103, which will not be described here for brevity. In step S104', the second sweetness detection model is established according to the effective apparent diffusion coefficient and the sweetness of the fruit sample, which is similar to establishing the first sweetness detection model, and additionally, the effect of the temperature is taken into consideration as well, so the apparent diffusion coefficients of the first reference object are also taken into account. Therefore, the second sweetness detection model represents a correlation between the sweetness of the fruit and two items, the effective apparent diffusion coefficient of the fruit and the apparent diffusion coefficient of the reference object.

According to the technical solution, the apparent diffusion coefficient of the second reference object is acquired when the apparent diffusion coefficients of the fruit to be detected are acquired without damage in step S110. The second reference object and the first reference object are of the same substance. Therefore, an error in detection results caused by different reference objects may be avoided. During magnetic resonance imaging in the step S110, the second reference object may be placed near the fruit to be detected. When pluralities of fruits to be detected are imaged, the second reference object may be placed among the fruits to be detected. Similarly, the second reference object and the fruits to be detected may be considered to be at a consistent temperature as being in the same environment. In step S130, the sweetness of the fruit to be detected is determined by using the second sweetness detection model; and the process is executed according to both the effective apparent diffusion coefficient of the fruit to be detected and the apparent diffusion coefficient of the second reference object.

According to the above technical solution, by using the apparent diffusion coefficient of the reference object, the effect of the temperature on sweetness detection is offset, and a more accurate sweetness detection result is acquired.

Illustratively, the second sweetness detection model is $Y=a2*x/x0+b2$, wherein Y represents the sweetness of the fruit; x represents the effective apparent diffusion coefficient of the fruit; x0 represents the apparent diffusion coefficient of the reference object; and a2 and b2 are parameters in the second sweetness detection model.

By using the second sweetness detection model, as the apparent diffusion coefficient of the reference object is introduced, the effect of the temperature difference on the detection result is avoided. The model is simpler, and calculation is easier.

Alternatively, the above reference objects (including the first reference object and the second reference object) are both aqueous solutions with the uniformity in apparent diffusion coefficient. The reference object may be contained by a vessel made of a non-metallic substance, for example, an organic glass vessel. As the reference object has the uniformity in apparent diffusion coefficient, a subsequent operation may be performed by directly using the apparent diffusion coefficient thereof without any further operation. The reference object may be a homogeneous solution of any substance. As magnetic resonance diffusion weighted imaging performs imaging on the diffusion phenomenon of the water molecules, the reference object may be water. The water has the highest uniformity in the apparent diffusion coefficient and is low in cost without pollution.

Figure 4:
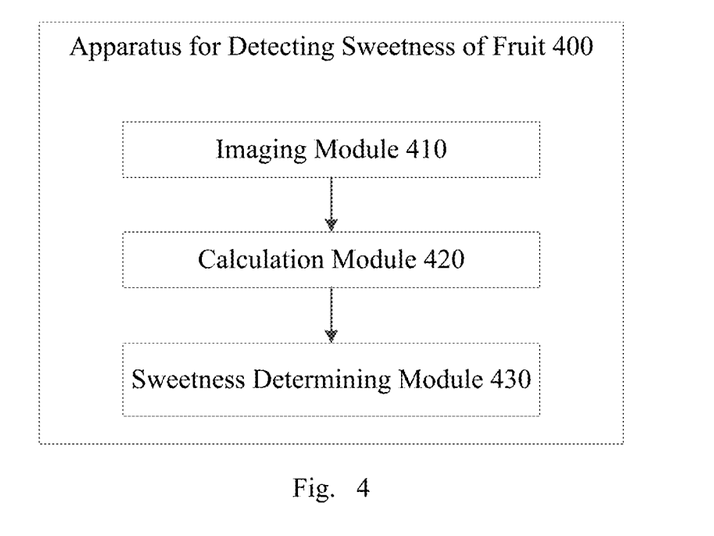
FIG. 4 shows a schematic block diagram of a device for detecting sweetness of a fruit according to an embodiment of the present invention.

According to another embodiment of the present invention, further provided is a device for detecting sweetness of a fruit. FIG. 4 is a schematic block diagram of a device 400 for detecting sweetness of a fruit according to an embodiment of the present invention. As shown in FIG. 4, the device 400 for detecting the sweetness of the fruit includes an imaging module 410, a calculation module 420 and a sweetness determining module 430.

The imaging module 410 is configured to nondestructively acquire apparent diffusion coefficients of the fruit to be detected by means of magnetic resonance diffusion weighted imaging.

The calculation module 420 is configured to determine an effective apparent diffusion coefficient of the fruit to be detected according to the apparent diffusion coefficients of the fruit to be detected.

The sweetness determining module 430 is configured to determine the sweetness of the fruit to be detected according to the effective apparent diffusion coefficient.

To sum up, each module in the device 400 for detecting the sweetness of the fruit is configured to specifically execute the corresponding step in the above method for detecting the sweetness of the fruit. By reviewing the above description with regard to the method, those of ordinary skill in the art may understand the specific implementations and the technical effects of the above device 400 for detecting the sweetness of the fruit.

According to another aspect of the present invention, further provided is a system for detecting sweetness of a fruit, including a processor and a memory, wherein computer program instructions for implementing various steps in the method for detecting the sweetness of the fruit according to the embodiments of the present invention are stored in the memory. The processor is configured to run the computer program instructions stored in the memory, so as to execute the corresponding steps in the method for detecting the sweetness of the fruit according to the embodiments of the present invention, and is configured to implement the imaging module 410, the calculation module 420 and the sweetness determining module 430 in the device for detecting the sweetness of the fruit according to the embodiments of the present invention.

In addition, according to yet another aspect of the present invention, a storage medium is provided. The storage medium stores program instructions, and when the program instructions are run by a computer or a processor, the computer or the processor executes corresponding steps of the method for detecting the sweetness of the fruit in the embodiments of the present invention and implements corresponding modules in the device for detecting the sweetness of the fruit in the embodiments of the present invention. The storage medium may include, for example, a storage component of a tablet computer, a hard disk of a personal computer, a read-only memory (ROM), an erasable programmable read-only memory (EPROM), a portable compact disc read-only memory (CD-ROM), and a USB memory, or any combination thereof. The computer-readable storage medium may be any combination of one or more computer-readable storage media.

Although exemplary embodiments have been described herein with reference to the accompanying drawings, it is to be understood that the exemplary embodiments described above are merely exemplary and are not intended to limit the scope of the present invention thereto. Various changes and modifications may be made therein by those of ordinary skill in the art without departing from the scope and spirit of the present invention. All the changes and modifications are intended to be included within the scope of the present invention as claimed in the appended claims.

Those of ordinary skill in the art may appreciate that the modules and algorithm steps of the examples described in conjunction with the embodiments disclosed herein can be implemented by electronic hardware, or a combination of computer software and electronic hardware. Whether these functions are executed by hardware or software depends on the specific application and design constraints of the technical solution. Those professional and skilled persons can use different methods to implement the described functions for each specific application, but such implementation should not be considered as going beyond the scope of the present invention.

In several embodiments provided in the disclosure, it should be understood that the disclosed devices and methods may be implemented in other ways. For example, the device embodiments described above are merely illustrative, for example, the division of the modules is merely a division of logical functions, and there may be other divisions in actual implementation, for example, a plurality of modules or components may be combined or integrated into another device, or some features may be ignored or not implemented.

Numerous specific details are set forth in the description provided herein. However, it can be appreciated that the embodiments of the present invention can be practiced without these specific details. In some examples, well-known methods, structures and techniques are not shown in detail in order not to obscure the understanding of this specification.

Similarly, it is to be appreciated that in order to simplify the present invention and aid in understanding one or more of the various aspects of the inventive, in the description of the exemplary embodiments of the present invention, the various features of the present invention are sometimes grouped together into a single embodiment, figure, or description thereof. However, the method of the present invention should not be interpreted as reflecting the intention that the claimed invention requires more features than those explicitly recited in each claim. More precisely, as reflected in the corresponding claims, the inventive points may lie in that the technical problems may be solved with the corresponding features less than all features of a single disclosed embodiment. Thus, the claims following the specific embodiments are explicitly incorporated into the specific embodiments, wherein each claim itself serves as a separate embodiment of the present invention.

Those skilled in the art will appreciate that all features disclosed in this specification (including the appended claims, abstract and drawings), and all processes or modules of any method or devices, may be combined in any combination, except that there is mutual exclusion therebetween. Each feature disclosed in this description (including the appended claims, abstract and drawings) may be replaced by an alternative feature serving the same, equivalent or similar purpose, unless indicated clearly otherwise.

Furthermore, those skilled in the art can appreciate that while some embodiments described herein include certain features included in other embodiments but not others, combinations of features of different embodiments means to be within the scope of the present invention and to form different embodiments. For example, in the claims, any of the claimed embodiments may be used in any combination.

Various component embodiments of the present invention may be implemented by hardware, or by software modules running on one or more processors, or by a combination thereof. Those skilled in the art will appreciate that some or all functions of some modules in the devices for detecting the sweetness of the fruit according to the embodiments of the present invention may be implemented in practice by a microprocessor or a digital signal processor (DSP). The present invention may also be implemented as a device program (for example, computer program and computer program product) for executing part or all of the methods described herein. Such a program for implementing the present invention may be stored on a computer-readable medium or may take the form of one or more signals. Such a signal may be downloaded from an Internet website, or provided by a carrier signal, or provided in any other form.

It should be noted that the above-described embodiments illustrate rather than limit the present invention and that alternative embodiments may be devised by those skilled in the art without departing from the scope of the appended claims. In the claims, any reference signs placed between parentheses shall not be construed as limiting the claims. The word "comprising" does not exclude the presence of elements or steps not listed in the claims. The word "a" or "an" preceding an element does not exclude the presence of a plurality of such elements. The present invention may be implemented by means of hardware including several different elements and by means of a suitably programmed computer. In the device claim enumerating several modules, several of the modules may be embodied in the same item of hardware. The use of words, "first", "second", "third", etc., does not indicate any order. These words may be interpreted as names.

The foregoing description, merely being specific embodiments of the present invention or descriptive of the specific embodiments, is not intended to limit the protection scope of the present invention. Any change or substitution, that may readily occur to those skilled in the art, within the technical scope disclosed in the present invention is intended to be encompassed within the protection scope of the present invention. The protection scope of the present invention shall be subject to the protection scope of the claims.

What is claimed is:

1. A method for detecting sweetness of a fruit, comprising:
    nondestructively acquiring apparent diffusion coefficients of the fruit to be detected by means of magnetic resonance diffusion weighted imaging;
    determining an effective apparent diffusion coefficient of the fruit to be detected according to the apparent diffusion coefficients of the fruit to be detected; and
    determining the sweetness of the fruit to be detected according to the effective apparent diffusion coefficient.

2. The method according to claim 1, characterized in that the method further comprises:
    nondestructively acquiring apparent diffusion coefficients of a fruit sample by means of magnetic resonance diffusion weighted imaging;

determining an effective apparent diffusion coefficient of the fruit sample according to the apparent diffusion coefficients of the fruit sample;

detecting sample sweetness of the fruit sample; and establishing a first sweetness detection model according to the effective apparent diffusion coefficient and the sample sweetness of the fruit sample, wherein the first sweetness detection model represents a correlation between the sweetness and the effective apparent diffusion coefficient;

wherein the sweetness of the fruit to be detected is determined according to the effective apparent diffusion coefficient by using the first sweetness detection model.

3. The method according to claim 2, characterized in that the first sweetness detection model is expressed as Y=a1*x+b1, wherein Y represents the sweetness; x represents the effective apparent diffusion coefficient; and a1 and b1 are parameters in the first sweetness detection model.

4. The method according to claim 1, characterized in that the method further comprises:

nondestructively acquiring apparent diffusion coefficients of a fruit sample and acquiring an apparent diffusion coefficient of a first reference object at the same time by means of magnetic resonance diffusion weighted imaging;

determining an effective apparent diffusion coefficient of the fruit sample according to the apparent diffusion coefficients of the fruit sample;

detecting sample sweetness of the fruit sample; and establishing a second sweetness detection model according to the apparent diffusion coefficient of the first reference object and the effective apparent diffusion coefficient and the sample sweetness of the fruit sample, wherein the second sweetness detection model represents a correlation between the sweetness of the fruit and two items, the effective apparent diffusion coefficient of the fruit and the apparent diffusion coefficient of the reference object;

wherein an apparent diffusion coefficient of a second reference object is acquired while the apparent diffusion coefficients of the fruit to be detected are nondestructively acquired; the second reference object is a same substance as the first reference object; and the sweetness of the fruit to be detected is determined further according to the apparent diffusion coefficient of the second reference object and by using the second sweetness detection model.

5. The method according to claim 4, characterized in that the second sweetness detection model is expressed as Y=a2*x/x0+b2, wherein Y represents the sweetness of the fruit; x represents the effective apparent diffusion coefficient of the fruit; x0 represents the apparent diffusion coefficient of the reference object; and a2 and b2 are parameters in the second sweetness detection model.

6. The method according to claim 4, characterized in that the reference object is water.

7. The method according to claim 1, characterized in that the apparent diffusion coefficients are expressed by an apparent diffusion coefficient image; and determining the effective apparent diffusion coefficient of the fruit to be detected according to the acquired apparent diffusion coefficients comprises:

performing image segmentation on the apparent diffusion coefficient image to determine a region of interest within pulp of the fruit to be detected, and calculating an average of values of pixels in the region of interest as the effective apparent diffusion coefficient.

8. A system for detecting sweetness of a fruit, comprising a processor and a memory, wherein computer program instructions are stored in the memory which are configured to perform a method for detecting the sweetness of the fruit executed by the processor, the method comprising:

nondestructively acquiring apparent diffusion coefficients of the fruit to be detected by means of magnetic resonance diffusion weighted imaging;

determining an effective apparent diffusion coefficient of the fruit to be detected according to the apparent diffusion coefficients of the fruit to be detected; and determining the sweetness of the fruit to be detected according to the effective apparent diffusion coefficient.

9. The system for detecting sweetness of a fruit according to claim 8, characterized in that the method further comprises:

nondestructively acquiring apparent diffusion coefficients of a fruit sample by means of magnetic resonance diffusion weighted imaging;

determining an effective apparent diffusion coefficient of the fruit sample according to the apparent diffusion coefficients of the fruit sample;

detecting sample sweetness of the fruit sample; and establishing a first sweetness detection model according to the effective apparent diffusion coefficient and the sample sweetness of the fruit sample, wherein the first sweetness detection model represents a correlation between the sweetness and the effective apparent diffusion coefficient;

wherein the sweetness of the fruit to be detected is determined according to the effective apparent diffusion coefficient by using the first sweetness detection model.

10. The system for detecting sweetness of a fruit according to claim 9, characterized in that the first sweetness detection model is expressed as Y=a1*x+b1, wherein Y represents the sweetness; x represents the effective apparent diffusion coefficient; and a1 and b1 are parameters in the first sweetness detection model.

11. The system for detecting sweetness of a fruit according to claim 8, characterized in that the method further comprises:

nondestructively acquiring apparent diffusion coefficients of a fruit sample and acquiring an apparent diffusion coefficient of a first reference object at the same time by means of magnetic resonance diffusion weighted imaging;

determining an effective apparent diffusion coefficient of the fruit sample according to the apparent diffusion coefficients of the fruit sample;

detecting sample sweetness of the fruit sample; and establishing a second sweetness detection model according to the apparent diffusion coefficient of the first reference object and the effective apparent diffusion coefficient and the sample sweetness of the fruit sample, wherein the second sweetness detection model represents a correlation between the sweetness of the fruit and two items, the effective apparent diffusion coefficient of the fruit and the apparent diffusion coefficient of the reference object;

wherein an apparent diffusion coefficient of a second reference object is acquired while the apparent diffusion coefficients of the fruit to be detected are nondestructively acquired; the second reference object is a same substance as the first reference object; and the sweetness of the fruit to be detected is determined further according to the apparent diffusion coefficient of the second reference object and by using the second sweetness detection model.

12. The system for detecting sweetness of a fruit according to claim 11, characterized in that the second sweetness detection model is expressed as Y=a2*x/x0+b2, wherein Y represents the sweetness of the fruit; x represents the effective apparent diffusion coefficient of the fruit; x0 represents the apparent diffusion coefficient of the reference object; and a2 and b2 are parameters in the second sweetness detection model.

13. A non-transitory storage medium, storing program instructions which are configured to perform, when executed by a processor, a method for detecting the sweetness of the fruit, the method comprising:
nondestructively acquiring apparent diffusion coefficients of the fruit to be detected by means of magnetic resonance diffusion weighted imaging;
determining an effective apparent diffusion coefficient of the fruit to be detected according to the apparent diffusion coefficients of the fruit to be detected; and
determining the sweetness of the fruit to be detected according to the effective apparent diffusion coefficient.

14. The non-transitory storage medium according to claim 13, characterized in that the method further comprises:
nondestructively acquiring apparent diffusion coefficients of a fruit sample by means of magnetic resonance diffusion weighted imaging;
determining an effective apparent diffusion coefficient of the fruit sample according to the apparent diffusion coefficients of the fruit sample;
detecting sample sweetness of the fruit sample; and
establishing a first sweetness detection model according to the effective apparent diffusion coefficient and the sample sweetness of the fruit sample, wherein the first sweetness detection model represents a correlation between the sweetness and the effective apparent diffusion coefficient;
wherein the sweetness of the fruit to be detected is determined according to the effective apparent diffusion coefficient by using the first sweetness detection model.

15. The non-transitory storage medium according to claim 14, characterized in that the first sweetness detection model is expressed as Y=a1*x+b1, wherein Y represents the sweetness; x represents the effective apparent diffusion coefficient; and a1 and b1 are parameters in the first sweetness detection model.

16. The non-transitory storage medium according to claim 13, characterized in that the method further comprises:
nondestructively acquiring apparent diffusion coefficients of a fruit sample and acquiring an apparent diffusion coefficient of a first reference object at the same time by means of magnetic resonance diffusion weighted imaging;
determining an effective apparent diffusion coefficient of the fruit sample according to the apparent diffusion coefficients of the fruit sample;
detecting sample sweetness of the fruit sample; and
establishing a second sweetness detection model according to the apparent diffusion coefficient of the first reference object and the effective apparent diffusion coefficient and the sample sweetness of the fruit sample, wherein the second sweetness detection model represents a correlation between the sweetness of the fruit and two items, the effective apparent diffusion coefficient of the fruit and the apparent diffusion coefficient of the reference object;
wherein an apparent diffusion coefficient of a second reference object is acquired while the apparent diffusion coefficients of the fruit to be detected are nondestructively acquired; the second reference object is a same substance as the first reference object; and the sweetness of the fruit to be detected is determined further according to the apparent diffusion coefficient of the second reference object and by using the second sweetness detection model.

17. The non-transitory storage medium according to claim 16, characterized in that the second sweetness detection model is expressed as Y=a2*x/x0+b2, wherein Y represents the sweetness of the fruit; x represents the effective apparent diffusion coefficient of the fruit; x0 represents the apparent diffusion coefficient of the reference object; and a2 and b2 are parameters in the second sweetness detection model.

18. The non-transitory storage medium according to claim 17, characterized in that the reference object is water.

19. The non-transitory storage medium according to claim 13, characterized in that the apparent diffusion coefficients are expressed by an apparent diffusion coefficient image; and determining the effective apparent diffusion coefficient of the fruit to be detected according to the acquired apparent diffusion coefficients comprises:
performing image segmentation on the apparent diffusion coefficient image to determine a region of interest within pulp of the fruit to be detected, and
calculating an average of values of pixels in the region of interest as the effective apparent diffusion coefficient.

* * * * *